United States Patent
Trock et al.

(12)

(10) Patent No.: US 9,018,893 B2
(45) Date of Patent: Apr. 28, 2015

(54) POWER CONTROL TECHNIQUES FOR AN ELECTRONIC DEVICE

(75) Inventors: Adam Trock, Burbank, CA (US); Jon Spurlin, Northridge, CA (US); Michael Ortega, Pasadena, CA (US); Seth Kazarians, Northridge, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1042 days.

(21) Appl. No.: 13/051,651

(22) Filed: Mar. 18, 2011

(65) Prior Publication Data

US 2012/0235485 A1   Sep. 20, 2012

(51) Int. Cl.
| | | |
|---|---|---|
| H02J 7/00 | (2006.01) | |
| H02J 7/34 | (2006.01) | |
| A61M 5/142 | (2006.01) | |

(52) U.S. Cl.
CPC ............. *H02J 7/34* (2013.01); *H02J 7/0021* (2013.01); *A61M 5/14244* (2013.01); *A61M 2205/8212* (2013.01); *A61M 2205/8237* (2013.01)

(58) Field of Classification Search
CPC ........................................................ H02J 7/0034
USPC ...................... 320/103; 307/18, 43–46, 64–66
See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |

(Continued)

FOREIGN PATENT DOCUMENTS

| | | |
|---|---|---|
| DE | 4329229 | 3/1995 |
| DE | 102009033309 A1 | 1/2011 |

(Continued)

OTHER PUBLICATIONS

PCT Search Report (PCT/US02/03299), Oct. 31, 2002, Medtronic Minimed, Inc.

(Continued)

*Primary Examiner* — Richard V Muralidar
(74) *Attorney, Agent, or Firm* — Ingrassia Fisher & Lorenz, P.C.

(57) ABSTRACT

A portable electronic device, such as a fluid infusion device, obtains its operating power from a primary battery and a secondary battery. The primary battery may be a replaceable battery, and the secondary battery may be a rechargeable battery that can be charged with the primary battery under certain conditions. The device utilizes a power management scheme that transitions between the primary battery and/or the secondary battery to prolong the useful life of the primary battery. The device may also generate an intelligent battery life indicator that displays an accurate representation of the remaining life of the primary battery.

12 Claims, 7 Drawing Sheets

(56) References Cited

U.S. PATENT DOCUMENTS

| | | | |
|---|---|---|---|
| 4,678,408 | A | 7/1987 | Nason et al. |
| 4,685,903 | A | 8/1987 | Cable et al. |
| 4,731,051 | A | 3/1988 | Fischell |
| 4,731,726 | A | 3/1988 | Allen, III |
| 4,781,798 | A | 11/1988 | Gough |
| 4,803,625 | A | 2/1989 | Fu et al. |
| 4,809,697 | A | 3/1989 | Causey, III et al. |
| 4,826,810 | A | 5/1989 | Aoki |
| 4,871,351 | A | 10/1989 | Feingold |
| 4,898,578 | A | 2/1990 | Rubalcaba, Jr. |
| 5,003,298 | A | 3/1991 | Havel |
| 5,011,468 | A | 4/1991 | Lundquist et al. |
| 5,019,974 | A | 5/1991 | Beckers |
| 5,050,612 | A | 9/1991 | Matsumura |
| 5,078,683 | A | 1/1992 | Sancoff et al. |
| 5,080,653 | A | 1/1992 | Voss et al. |
| 5,097,122 | A | 3/1992 | Colman et al. |
| 5,100,380 | A | 3/1992 | Epstein et al. |
| 5,101,814 | A | 4/1992 | Palti |
| 5,108,819 | A | 4/1992 | Heller et al. |
| 5,153,827 | A | 10/1992 | Coutre et al. |
| 5,165,407 | A | 11/1992 | Wilson et al. |
| 5,247,434 | A | 9/1993 | Peterson et al. |
| 5,262,035 | A | 11/1993 | Gregg et al. |
| 5,262,305 | A | 11/1993 | Heller et al. |
| 5,264,104 | A | 11/1993 | Gregg et al. |
| 5,264,105 | A | 11/1993 | Gregg et al. |
| 5,284,140 | A | 2/1994 | Allen et al. |
| 5,299,571 | A | 4/1994 | Mastrototaro |
| 5,307,263 | A | 4/1994 | Brown |
| 5,317,506 | A | 5/1994 | Coutre et al. |
| 5,320,725 | A | 6/1994 | Gregg et al. |
| 5,322,063 | A | 6/1994 | Allen et al. |
| 5,338,157 | A | 8/1994 | Blomquist |
| 5,339,821 | A | 8/1994 | Fujimoto |
| 5,341,291 | A | 8/1994 | Roizen et al. |
| 5,350,411 | A | 9/1994 | Ryan et al. |
| 5,356,786 | A | 10/1994 | Heller et al. |
| 5,357,427 | A | 10/1994 | Langen et al. |
| 5,368,562 | A | 11/1994 | Blomquist et al. |
| 5,370,622 | A | 12/1994 | Livingston et al. |
| 5,371,687 | A | 12/1994 | Holmes, II et al. |
| 5,376,070 | A | 12/1994 | Purvis et al. |
| 5,390,671 | A | 2/1995 | Lord et al. |
| 5,391,250 | A | 2/1995 | Cheney, II et al. |
| 5,403,700 | A | 4/1995 | Heller et al. |
| 5,411,647 | A | 5/1995 | Johnson et al. |
| 5,482,473 | A | 1/1996 | Lord et al. |
| 5,485,408 | A | 1/1996 | Blomquist |
| 5,497,772 | A | 3/1996 | Schulman et al. |
| 5,505,709 | A | 4/1996 | Funderburk et al. |
| 5,543,326 | A | 8/1996 | Heller et al. |
| 5,569,186 | A | 10/1996 | Lord et al. |
| 5,569,187 | A | 10/1996 | Kaiser |
| 5,573,506 | A | 11/1996 | Vasko |
| 5,582,593 | A | 12/1996 | Hultman |
| 5,586,553 | A | 12/1996 | Halili et al. |
| 5,593,390 | A | 1/1997 | Castellano et al. |
| 5,593,852 | A | 1/1997 | Heller et al. |
| 5,594,638 | A | 1/1997 | Iliff |
| 5,609,060 | A | 3/1997 | Dent |
| 5,626,144 | A | 5/1997 | Tacklind et al. |
| 5,630,710 | A | 5/1997 | Tune et al. |
| 5,631,503 | A * | 5/1997 | Cioffi ................. 307/66 |
| 5,643,212 | A | 7/1997 | Coutre et al. |
| 5,660,163 | A | 8/1997 | Schulman et al. |
| 5,660,176 | A | 8/1997 | Iliff |
| 5,665,065 | A | 9/1997 | Colman et al. |
| 5,665,222 | A | 9/1997 | Heller et al. |
| 5,685,844 | A | 11/1997 | Marttila |
| 5,687,734 | A | 11/1997 | Dempsey et al. |
| 5,704,366 | A | 1/1998 | Tacklind et al. |
| 5,747,891 | A * | 5/1998 | Williams ................. 307/87 |
| 5,750,926 | A | 5/1998 | Schulman et al. |
| 5,754,111 | A | 5/1998 | Garcia |
| 5,764,159 | A | 6/1998 | Neftel |
| 5,772,635 | A | 6/1998 | Dastur et al. |
| 5,779,665 | A | 7/1998 | Mastrototaro et al. |
| 5,788,669 | A | 8/1998 | Peterson |
| 5,791,344 | A | 8/1998 | Schulman et al. |
| 5,800,420 | A | 9/1998 | Gross et al. |
| 5,807,336 | A | 9/1998 | Russo et al. |
| 5,814,015 | A | 9/1998 | Gargano et al. |
| 5,822,715 | A | 10/1998 | Worthington et al. |
| 5,832,448 | A | 11/1998 | Brown |
| 5,835,366 | A * | 11/1998 | Pleso et al. ................. 363/59 |
| 5,840,020 | A | 11/1998 | Heinonen et al. |
| 5,861,018 | A | 1/1999 | Feierbach et al. |
| 5,868,669 | A | 2/1999 | Iliff |
| 5,871,465 | A | 2/1999 | Vasko |
| 5,879,163 | A | 3/1999 | Brown et al. |
| 5,885,245 | A | 3/1999 | Lynch et al. |
| 5,897,493 | A | 4/1999 | Brown |
| 5,899,855 | A | 5/1999 | Brown |
| 5,904,708 | A | 5/1999 | Goedeke |
| 5,913,310 | A | 6/1999 | Brown |
| 5,917,346 | A | 6/1999 | Gord |
| 5,918,603 | A | 7/1999 | Brown |
| 5,925,021 | A | 7/1999 | Castellano et al. |
| 5,933,136 | A | 8/1999 | Brown |
| 5,935,099 | A | 8/1999 | Peterson et al. |
| 5,940,801 | A | 8/1999 | Brown |
| 5,956,501 | A | 9/1999 | Brown |
| 5,960,403 | A | 9/1999 | Brown |
| 5,965,380 | A | 10/1999 | Heller et al. |
| 5,972,199 | A | 10/1999 | Heller et al. |
| 5,978,236 | A | 11/1999 | Faberman et al. |
| 5,997,476 | A | 12/1999 | Brown |
| 5,999,848 | A | 12/1999 | Gord et al. |
| 5,999,849 | A | 12/1999 | Gord et al. |
| 6,009,339 | A | 12/1999 | Bentsen et al. |
| 6,032,119 | A | 2/2000 | Brown et al. |
| 6,043,437 | A | 3/2000 | Schulman et al. |
| 6,081,736 | A | 6/2000 | Colvin et al. |
| 6,083,710 | A | 7/2000 | Heller et al. |
| 6,087,740 | A * | 7/2000 | Williams ................. 307/125 |
| 6,088,608 | A | 7/2000 | Schulman et al. |
| 6,101,478 | A | 8/2000 | Brown |
| 6,103,033 | A | 8/2000 | Say et al. |
| 6,119,028 | A | 9/2000 | Schulman et al. |
| 6,120,676 | A | 9/2000 | Heller et al. |
| 6,121,009 | A | 9/2000 | Heller et al. |
| 6,134,461 | A | 10/2000 | Say et al. |
| 6,143,164 | A | 11/2000 | Heller et al. |
| 6,162,611 | A | 12/2000 | Heller et al. |
| 6,175,752 | B1 | 1/2001 | Say et al. |
| 6,183,412 | B1 | 2/2001 | Benkowski et al. |
| 6,246,992 | B1 | 6/2001 | Brown |
| 6,259,937 | B1 | 7/2001 | Schulman et al. |
| 6,329,161 | B1 | 12/2001 | Heller et al. |
| 6,408,330 | B1 | 6/2002 | DeLaHuerga |
| 6,424,847 | B1 | 7/2002 | Mastrototaro et al. |
| 6,472,122 | B1 | 10/2002 | Schulman et al. |
| 6,484,045 | B1 | 11/2002 | Holker et al. |
| 6,484,046 | B1 | 11/2002 | Say et al. |
| 6,485,465 | B2 | 11/2002 | Moberg et al. |
| 6,503,381 | B1 | 1/2003 | Gotoh et al. |
| 6,514,718 | B2 | 2/2003 | Heller et al. |
| 6,544,173 | B2 | 4/2003 | West et al. |
| 6,553,263 | B1 | 4/2003 | Meadows et al. |
| 6,554,798 | B1 | 4/2003 | Mann et al. |
| 6,558,320 | B1 | 5/2003 | Causey, III et al. |
| 6,558,351 | B1 | 5/2003 | Steil et al. |
| 6,560,741 | B1 | 5/2003 | Gerety et al. |
| 6,565,509 | B1 | 5/2003 | Say et al. |
| 6,579,690 | B1 | 6/2003 | Bonnecaze et al. |
| 6,591,125 | B1 | 7/2003 | Buse et al. |
| 6,592,745 | B1 | 7/2003 | Feldman et al. |
| 6,605,200 | B1 | 8/2003 | Mao et al. |
| 6,605,201 | B1 | 8/2003 | Mao et al. |
| 6,607,658 | B1 | 8/2003 | Heller et al. |
| 6,616,819 | B1 | 9/2003 | Liamos et al. |
| 6,618,934 | B1 | 9/2003 | Feldman et al. |
| 6,623,501 | B2 | 9/2003 | Heller et al. |

(56) References Cited

U.S. PATENT DOCUMENTS

| | | | |
|---|---|---|---|
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,332,896 B2 * | 2/2008 | Shin et al. ................ 307/80 |
| 7,396,330 B2 | 7/2008 | Banet et al. |
| 7,621,893 B2 | 11/2009 | Moberg et al. |
| 7,737,581 B2 * | 6/2010 | Spurlin et al. ............ 307/66 |
| 2001/0044731 A1 | 11/2001 | Coffman et al. |
| 2001/0054878 A1 | 12/2001 | Odaohhara |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |

FOREIGN PATENT DOCUMENTS

| | | |
|---|---|---|
| EP | 0319268 | 11/1988 |
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkami K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.

(56) References Cited

OTHER PUBLICATIONS (MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump Users Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

(56) References Cited

OTHER PUBLICATIONS

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nut. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

POWER CONTROL TECHNIQUES FOR AN ELECTRONIC DEVICE

TECHNICAL FIELD

Embodiments of the subject matter described herein relate generally to power control, management, and monitoring for electronic devices, such as fluid infusion pumps, analyte sensor devices, mobile phones, and the like. More particularly, embodiments of the subject matter relate to power management and battery life indication schemes for a portable electronic device having a primary battery and a secondary battery.

BACKGROUND

The prior art is replete with various types of electronic devices. For example, portable medical devices are useful for patients that have conditions that must be monitored on a continuous or frequent basis. In this regard, diabetics are usually required to modify and monitor their daily lifestyle to keep their blood glucose (BG) in balance. Some diabetics use portable insulin pump systems that are designed to deliver accurate and measured doses of insulin via infusion sets (an infusion set delivers the insulin through a small diameter tube that terminates at, e.g., a cannula inserted under the patient's skin). Portable insulin pumps are usually powered by either an alkaline battery, a lithium-ion battery, or a rechargeable battery.

One drawback with battery operated devices is the inability to utilize all of the energy stored in the battery due to the natural voltage decay associated with energy depletion. This particular problem is most prevalent with alkaline batteries, which tend to suffer a drop in voltage after a relatively short period of time even though an adequate amount of stored energy remains. Lithium and nickel-metal hydride (NiMH) batteries tend to maintain a more stable voltage over time, which generally allows for a higher percentage of the stored energy to be utilized, relative to the amount of stored energy typically utilized with alkaline batteries. Although lithium and NiMH batteries maintain a very stable voltage over time, they suffer from a sharp voltage drop at the end of life. Predicting when this drop will occur is very difficult and often requires a great deal of testing and characterization to allow for a sufficient user warning before the actual end of the battery life.

The remaining amount of battery life is often displayed on an electronic device in the form of a graphical icon, an indicator, a graph, or the like. Conventional battery life indicators used with consumer devices (e.g., mobile phones, digital media players, and video game devices) can be inaccurate and imprecise. Moreover, conventional battery life indicators may not use a proportional time scale for purposes of representing the remaining amount of battery life. For example, if the total lifespan of a replaceable battery is ten days for a given electronic device, a conventional battery life indicator might indicate full battery capacity for eight days, and thereafter indicate a quick decrease in battery capacity. Thus, it would be desirable to have a battery life indicator that accurately and proportionately indicates the remaining amount of battery life relative to actual runtime of the battery.

BRIEF SUMMARY

An exemplary embodiment of a power management method for an electronic device having a primary battery and a secondary battery is provided. The method involves operating the electronic device in different power phases: a first power phase during which the primary battery provides energy to support all functions of the electronic device; a second power phase during which the primary battery provides energy to support basic functions of the electronic device, and during which the secondary battery provides energy to support high power functions of the electronic device; and a third power phase during which the secondary battery provides energy to support all functions of the electronic device.

Also provided is an exemplary embodiment of a power management method for an electronic device having a primary battery, a secondary battery, a voltage converter to convert an output voltage of the primary battery to a main supply voltage for the electronic device, a first voltage rail to provide operating voltage for basic functions of the electronic device, a second voltage rail to provide operating voltage for high power functions of the electronic device, and a power distribution system. The method monitors the main supply voltage during operation of the electronic device and arranges the power distribution system in an appropriate manner. The method initially operates the power distribution system in a first power phase such that the primary battery provides voltage for the first voltage rail and the second voltage rail. The method transitions the power distribution system from the first power phase to a second power phase such that the primary battery provides voltage for the first voltage rail, and such that the secondary battery provides voltage for the second voltage rail. Transitioning from the first power phase to the second power phase is triggered when the main supply voltage falls below a threshold value while monitored during the first power phase. The method also transitions the power distribution system from the second power phase to a third power phase such that the secondary battery provides voltage for the first voltage rail and the second voltage rail. Transitioning from the second power phase to the third power phase is triggered when the main supply voltage falls below the threshold value while monitored during the second power phase.

An exemplary embodiment of a power distribution system for a portable electronic device is also provided. The power distribution system includes: a first voltage rail to provide operating voltage for basic functions of the electronic device; a second voltage rail to provide operating voltage for high power functions of the electronic device; a primary battery coupled in a selectable manner to the first voltage rail and the second voltage rail; a secondary battery coupled in a selectable manner to the first voltage rail and the second voltage rail; a selection architecture coupled to the first voltage rail, the second voltage rail, the primary battery, and the secondary battery; and a control module to regulate operation of the selection architecture in accordance with different power phases.

An exemplary embodiment of a method of controlling a battery life indicator for a primary battery of an electronic device is also presented. The method involves: monitoring a battery voltage of the primary battery; obtaining at least one operating parameter of the electronic device other than the battery voltage of the primary battery; and generating the battery life indicator with characteristics that represent remaining battery life of the primary battery, wherein the characteristics are dictated by the monitored battery voltage and the obtained at least one operating parameter.

Also provided is an exemplary embodiment of a method of controlling a battery life indicator for an electronic device having a primary battery and a secondary battery. The electronic device operates in either a first power phase during which only the primary battery supports functions of the electronic device, a second power phase during which both the primary battery and the secondary battery support functions of the electronic device, or a third power phase during which only the secondary battery supports functions of the electronic device. The method involves: determining whether the electronic device is operating in the first power phase, the second power phase, or the third power phase, resulting in a determined power phase; obtaining a runtime measurement for the primary battery; and generating the battery life indicator with characteristics that represent remaining battery life of the primary battery, wherein the characteristics are controlled by the determined power phase and the obtained runtime measurement.

An exemplary embodiment of a battery monitor system for an electronic device having a primary battery and a secondary battery is also presented. The battery monitor system includes: a voltage monitor that monitors a battery voltage of the primary battery; a control module to operate the electronic device in a designated power phase corresponding to either a first power phase, a second power phase, or a third power phase; a runtime counter to maintain a runtime measurement for the primary battery; and a battery life indicator controller coupled to the voltage monitor, the control module, and the runtime counter to generate a battery life indicator for the electronic device that indicates an amount of remaining battery life of the primary battery. The amount of remaining battery life is governed by at least two of: the battery voltage of the primary battery; the designated power phase; and the runtime measurement.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
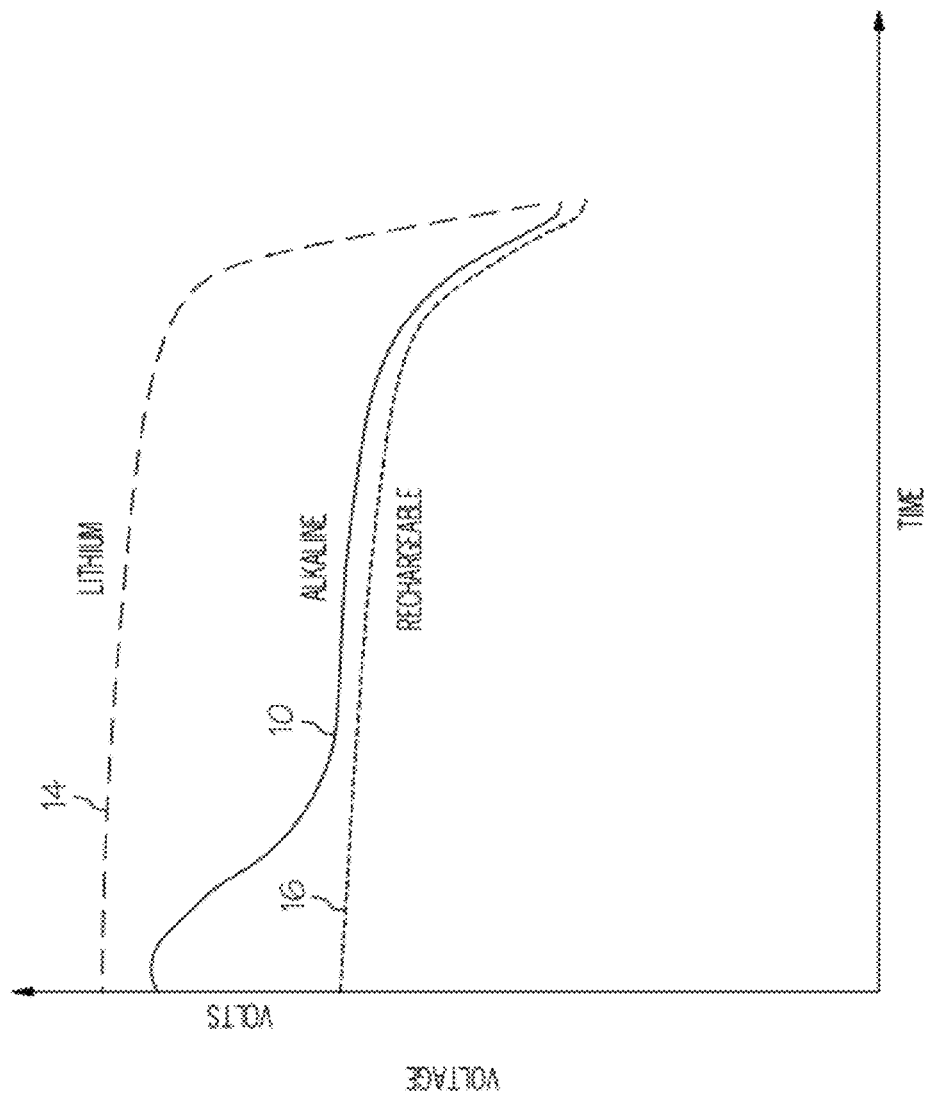
FIG. 1 illustrates voltage level versus time provided by different types of batteries.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

The subject matter described here relates to battery systems, power management, displayed battery life indicators, and related processes that may be carried out by an electronic device. The electronic device will typically be a portable or mobile device, although portability is not a requirement. In practice, a portable electronic device may be a personal medical device (e.g., a fluid infusion device such as an insulin pump, a glucose sensor, a transmitter, a pacemaker, or any type of medical monitor), a mobile phone, a handheld computer, a digital media player, a video game device, an electronic book reader, or the like. Indeed, the subject matter presented here applies to any electronic device that is powered or can be powered by a removable primary battery and a secondary battery.

Although certain exemplary embodiments are described below in the context of a fluid infusion device, the concepts and methodologies need not be limited to that particular application. Moreover, for the sake of brevity, conventional techniques and technologies related to infusion system operation, insulin pump and/or infusion set operation, blood glucose sensing and monitoring, and other functional aspects of the systems (and the individual operating components of the systems) may not be described in detail here. Examples of infusion pumps and/or related pump drive systems used to administer insulin and other medications may be of the type described in, but not limited to, U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; and 7,621,893; which are herein incorporated by reference.

Many portable electronic devices are powered by one or more batteries. The standard AA battery is commonly used in a wide variety of electronic devices, including portable medical devices. The nominal voltage of a AA battery is typically within the range of about 1.25 to 1.65 volts, depending upon the chemistry type of the AA battery. Electronic devices are often powered by alkaline, nickel-cadmium (NiCad), lithium, or lithium-ion batteries. Different types of batteries exhibit different voltage characteristics over time. In this regard, FIG. 1 illustrates voltage level versus time provided by different types of batteries.

The plot 10 in FIG. 1 represents a typical voltage curve for a replaceable alkaline battery. The alkaline battery begins its life at a relatively high voltage, e.g., approximately 1.55 volts for a AA size battery, but its initial voltage drops after a short amount of time. Thereafter, its voltage decreases somewhat gradually over time. In contrast, a lithium battery is capable of providing a much higher initial voltage and sustaining relatively high voltage for a long period of time. However, as illustrated by the plot 14 in FIG. 1, a lithium battery typically experiences a sharp voltage drop at or near its end of life. This rapid drop in voltage is represented by the "knee" characteristic of the plot 14. If a lithium battery is being used in a portable electronic device, a user of the portable electronic device may have only a short amount of time after receiving a low battery message before the portable electronic device loses power. A rechargeable battery can be a good economic solution for an owner of a portable electronic device. Rather than buying new replaceable batteries, the user may utilize household current to charge a rechargeable battery after the battery has expended its energy. Many portable electronic devices cannot utilize rechargeable batteries because the initial voltage supplied by rechargeable batteries is too low to satisfy the operating requirements of those devices. The rechargeable battery has characteristics similar to the alkaline battery in terms of how long it can power a device, but as illustrated by the plot 16 in FIG. 1, the initial voltage supplied by the rechargeable battery is lower than the initial voltage supplied by the alkaline battery.

The electronic device described below employs a primary battery (which is a replaceable battery in the exemplary embodiment) and a secondary battery (which is a "permanent" or non-replaceable rechargeable battery in the exemplary embodiment). The electronic device carries out a power management scheme that enables the electronic device to utilize most of the stored energy in the primary battery before it needs to be replaced. The power management scheme allows the electronic device to efficiently and interchangeably use alkaline, lithium, and other battery types as the primary battery. In practice, the power management scheme could also leverage some of the features described in U.S. Pat. No. 7,737,581, the relevant content of which is incorporated by reference herein.

Figure 2:
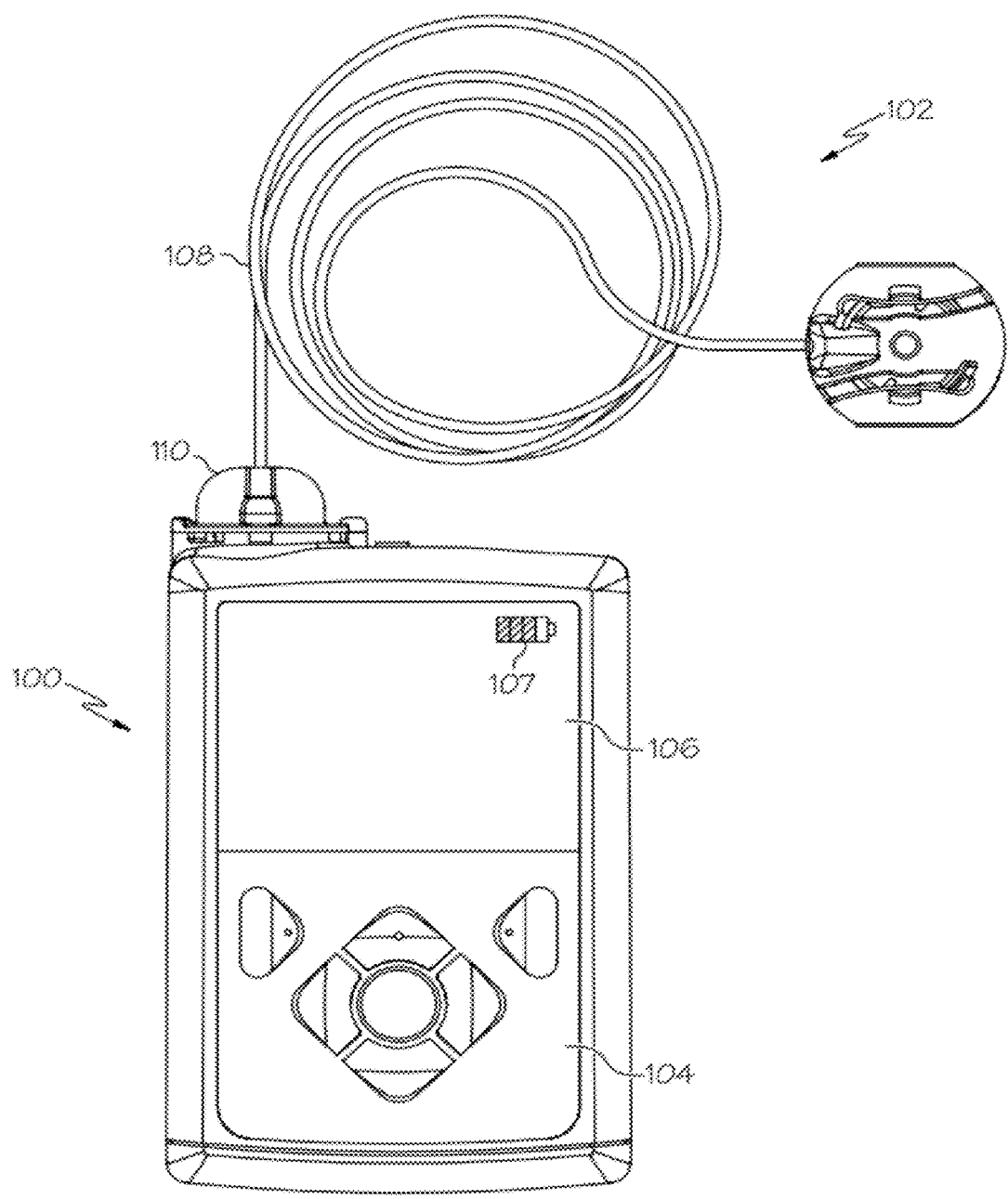
FIG. 2 is a plan view of an exemplary embodiment of a fluid infusion device.

As mentioned above, a portable medical device such as a fluid infusion device could leverage the power management and battery life indication techniques presented here. In this regard, FIG. 2 is a plan view of an exemplary embodiment of a fluid infusion device 100. FIG. 2 also shows an infusion set 102 coupled to the fluid infusion device 100. The fluid infusion device 100 is designed to be carried or worn by the patient. The fluid infusion device 100 may leverage a number of conventional features, components, elements, and characteristics of existing fluid infusion devices. For example, the fluid infusion device 100 may incorporate some of the features, components, elements, and/or characteristics described in U.S. Pat. Nos. 6,485,465 and 7,621,893, the relevant content of which is incorporated by reference herein.

This embodiment shown in FIG. 2 includes a user interface 104 having several buttons that can be activated by the user. These buttons can be used to administer a bolus of insulin, to change therapy settings, to change user preferences, to select display features, and the like. Although not required, the illustrated embodiment of the fluid infusion device 100 includes a display element 106. The display element 106 can be used to present various types of information or data to the user, such as, without limitation: the current glucose level of the patient; the time; a graph or chart of the patient's glucose level versus time; device status indicators, including a battery life indicator 107; etc. In some embodiments, the display element 106 is realized as a touch screen display element and, therefore, the display element 106 also serves as a user interface component.

The fluid infusion device 100 accommodates a fluid reservoir (hidden from view in FIG. 2) for the fluid to be delivered to the user. Activation of an internal motor results in actuation of the fluid reservoir, which in turn delivers the fluid. A length of tubing 108 is the flow path that couples the fluid reservoir to the infusion set 102. The tubing 108 extends from the fluid infusion device 100 to the infusion set 102, which provides a fluid pathway with the body of the user. A removable cap or fitting 110 is suitably sized and configured to accommodate replacement of fluid reservoirs (which are typically disposable) as needed. In this regard, the fitting 110 is designed to accommodate the fluid path from the fluid reservoir to the tubing 108.

Figure 3:
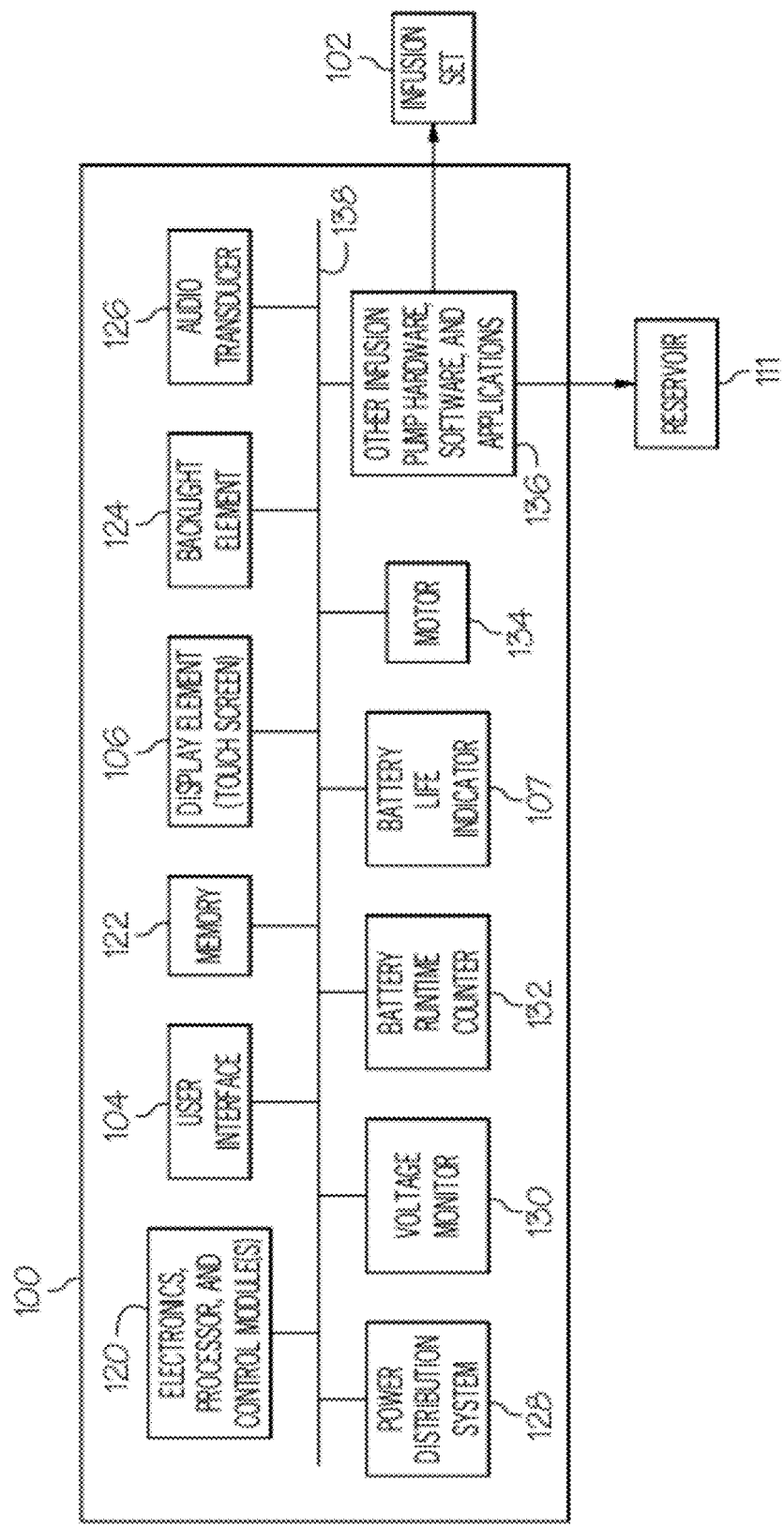
FIG. 3 is a schematic block diagram representation of an exemplary embodiment of a fluid infusion device.

As mentioned previously, the fluid infusion device 100 is suitably configured to support a number of power and battery related techniques, processes, and methodologies. In practice, the fluid infusion device 100 includes one or more electronics modules, processing logic, software applications, and/or other features that are used to carry out the various operating processes described here. In this regard, FIG. 3 is a schematic block diagram representation of an exemplary embodiment of the fluid infusion device 100. FIG. 3 depicts some previously-described elements of the fluid infusion device 100 as functional blocks or modules, namely, the display element 106; the user interface 104; and the battery life indicator 107. FIG. 3 also depicts a fluid reservoir 111 and the infusion set 102 in block format. This particular embodiment of the fluid infusion device 100 also includes, without limitation: one or more electronics, processor, and control modules 120; a suitable amount of memory 122; a backlight element 124, which may be integrated with the display element 106; an audio transducer element 126; a power distribution system 128; a voltage monitor 130 (which in certain embodiments may be realized as a voltage supervisor); a battery runtime counter 132; a motor 134 to actuate the fluid reservoir 111; and other infusion pump hardware, software, and applications 136. The elements of the fluid infusion device 100 may be coupled together via an interconnection architecture 138 or arrangement that facilitates transfer of data, commands, power, etc.

The module(s) 120 may represent any number of electronics modules, processor modules, logical elements, controllers, and/or control modules of the fluid infusion device 100. The module(s) 120 may include or be implemented with a general purpose processor, a plurality of cooperating processor devices, a content addressable memory, a digital signal processor, an application specific integrated circuit, a field programmable gate array, any suitable programmable logic device, discrete gate or transistor logic, discrete hardware components, or any combination designed to perform the functions described here. A processor device may be realized as a microprocessor, a controller, a microcontroller, or a state machine. Moreover, a processor device may be implemented as a combination of computing devices, e.g., a combination of a digital signal processor and a microprocessor, a plurality of microprocessors, one or more microprocessors in conjunction with a digital signal processor core, or any other such configuration.

As described in more detail below, the module(s) 120 may be responsible for operating the fluid infusion device 100 in various power phases or modes to take better advantage of stored battery energy. In this regard, the module(s) 120 may be used to monitor and/or measure operating parameters of the fluid infusion device 100 (such as voltage levels), and regulate operation of switches, multiplexers, voltage converters, a battery charger, and the like. The module(s) 120 may also be responsible for controlling and generating the battery life indicator 107 in accordance with the methodologies described below. Moreover, a functional or logical module/component of the fluid infusion device 100 might be realized by, implemented with, and/or controlled by processing logic maintained by or included with the module(s) 120. For example, the display element 106, the user interface 104, the motor 134, and/or the infusion pump hardware, software, and applications 136 (or portions thereof) may be implemented in or controlled by the module(s) 120.

The memory 122 may be realized as RAM memory, flash memory, EPROM memory, EEPROM memory, registers, a hard disk, a removable disk, a CD-ROM, or any other form of storage medium known in the art. In this regard, the memory 122 can be coupled to the module(s) 120 such that the module(s) 120 can read information from, and write information to, the memory 122. In the alternative, the memory 122 may be integral to the module(s) 120. As an example, a processor and the memory 122 may reside in an ASIC. In practice, a functional or logical module/component of the fluid infusion device 100 might be realized using program code that is maintained in the memory 122. Moreover, the memory 122 can be used to store data utilized to support the operation of the fluid infusion device 100, including, without limitation, voltage measurements, operating status data, battery voltage thresholds, and the like (as will become apparent from the following description).

The user interface 104 may include a variety of items such as, without limitation: a keypad, keys, buttons, a keyboard, switches, knobs (which may be rotary or push/rotary), a touchpad, a microphone suitably adapted to receive voice commands, a joystick, a pointing device, an alphanumeric character entry device or touch element, a trackball, a motion sensor, a lever, a slider bar, a virtual writing tablet, or any device, component, or function that enables the user to select options, input information, or otherwise control the operation of the fluid infusion device 100. In this context, the user interface 104 may cooperate with or include a touch screen display element 106. The user interface 104 allows a user to control the delivery of fluid via the infusion set 102.

The display element 106 represents the primary graphical interface of the fluid infusion device 100. The display element 106 may leverage known plasma, liquid crystal display (LCD), thin film transistor (TFT), and/or other display technologies. The actual size, resolution, and operating specifications of the display element 106 can be selected to suit the needs of the particular application. Notably, the display element 106 may include or be realized as a touch screen display element that can accommodate touch screen techniques and technologies. In practice, the display element 106 may be driven by a suitable display driver to enable the fluid infusion device 100 to display physiological patient data, status information, clock information, alarms, alerts, and/or other information and data received or processed by the fluid infusion device 100. For example, the display element 106 could be used to display a graphical representation of the battery life indicator 107, as shown in FIG. 2.

The fluid infusion device 100 may include the backlight element 124 integrated with or cooperating with the display element 106. The backlight element 124 is illuminated when needed (or when commanded to do so) to enhance the readability of the contents rendered on the display element 106. As explained in more detail below, operation of the backlight element 124 may be considered to be a high power function of the fluid infusion device 100 because activation of the backlight element 124 typically requires a high amount of electrical current, which consumes a relatively high amount of energy. Consequently, the backlight element 124 is coupled to a high power voltage rail of the fluid infusion device 100 (the voltage rail is not shown in FIG. 3).

The fluid infusion device 100 may also include one or more audio transducer elements 126 to generate sound as needed or desired. In practice, the audio transducer element 126 requires a relatively high amount of energy to be driven properly (in certain embodiments, the audio transducer element 126 may be realized as a piezoelectric transducer, a speaker, or the like). Accordingly, operation of the audio transducer element 126 may be considered to be a high power function of the fluid infusion device 100 because activation of the audio transducer element 126 typically requires a high amount of electrical current, which consumes a relatively high amount of energy. Consequently, the audio transducer element 126 is also coupled to the high power voltage rail of the fluid infusion device 100.

The power distribution system 128 is responsible for various power management and battery selection processes carried out by the fluid infusion device 100. It should be appreciated that a module 120, the voltage monitor 130, the battery runtime counter 132, and/or some of the other infusion pump hardware, software, and applications 136 may be considered to be a part of the power distribution system 128. During operation of the fluid infusion device 100, the power distribution system 128 is controlled and arranged to transition between different power phases (the different power phases are associated with primary battery operation and/or secondary battery operation). An exemplary embodiment of the power distribution system 128 is described in more detail below with reference to FIG. 4.

The voltage monitor 130 is suitably configured to monitor one or more voltage levels of the fluid infusion device 100. In this regard, the voltage monitor 130 may be coupled to one or more voltage rails, voltage buses, electrical nodes, or the like for purposes of detecting and measuring the respective voltage. Alternatively (or additionally), the voltage monitor 130 could be incorporated into a power supply, a voltage converter, a device driver, or the like. For example, and without limitation, the voltage monitor 130 could monitor the primary battery voltage, the secondary battery voltage, the output of a voltage converter that converts the primary battery voltage, the output of a voltage converter that converts the secondary battery voltage, a main supply voltage rail, a high power voltage rail, a low power voltage rail, or the like. When monitoring the primary battery for generation of the battery life indicator 107, the voltage monitor 130 may measure the primary battery voltage in a loaded state or in a virtually unloaded state (where loads that are not necessary for voltage measurement are disconnected from the primary battery). Although this description refers to a single voltage monitor 130, an embodiment of the fluid infusion device 100 may utilize a plurality of voltage monitors 130 if so desired.

The battery runtime counter 132 keeps track of a runtime measurement for the primary battery (and, in certain embodiments, the secondary battery). This enables the fluid infusion device 100 to generate the battery life indicator 107 in a manner that is influenced by the runtime measurement. In practice, the battery runtime counter 132 may be realized as a timer that is reset whenever a primary battery is installed. The battery runtime counter 132 may keep track of the runtime in any desired unit or units of time, e.g., minutes, hours, days, or weeks. Alternatively, the battery runtime counter 132 could measure the runtime of the battery using any arbitrary reference system or unit of measurement.

An exemplary implementation of the battery life indicator 107 is shown in FIG. 2. For this embodiment, the battery life indicator 107 is realized as a dynamic graphical icon that is rendered on the display element 106. The illustrated embodiment of the battery life indicator 107 includes multiple segments (four segments for this example). Moreover, each segment of the battery life indicator 107 is intended to represent a proportional amount of remaining battery life. Thus, if all four segments are displayed, then the battery could have up to 100% of its total life remaining. In contrast, only one displayed segment might indicate a low battery condition, a limited amount of remaining runtime, or a relatively low percentage of battery life remaining.

It should be appreciated that other embodiments may utilize more or less than four icon segments. Yet other embodiments could employ a different scheme to represent the remaining battery life of the battery using the battery life indicator 107. For example, an embodiment of the battery life indicator 107 could be rendered in a continuous or virtually continuous manner that does not rely on distinct segments per se. As another example, an embodiment of the battery life indicator 107 could use alphanumeric characters that indicate the amount of remaining runtime and/or a percentage of remaining battery life. Yet other embodiments of the battery life indicator 107 could implement other graphical schemes or icons to represent the remaining battery life.

The motor 134 represents the fluid delivery or drive motor of the fluid infusion device 100. The motor 134 is controlled and activated to actuate the fluid reservoir 111 to deliver fluid via the infusion set 102. The motor 134 may also be controlled and activated to rewind the actuator of the fluid reservoir 111 to accommodate removal and replacement of the fluid reservoir 111. As explained in more detail below, operation of the motor 134 may be considered to be a high power function of the fluid infusion device 100 because activation of the motor 134 typically requires a high amount of electrical current, which consumes a relatively high amount of energy. Consequently, the motor 134 is coupled to a high power voltage rail of the fluid infusion device 100 (the voltage rail is not shown in FIG. 3).

The infusion pump hardware, software, and applications 136 are utilized to carry out other fluid infusion features, operations, and functionality that may not be the focus of this description. Thus, the infusion pump hardware, software, and applications 136 may include or cooperate with the infusion set 102 and/or the fluid reservoir 111 (as described above). It should be appreciated that the infusion pump hardware, software, and applications 136 may leverage known techniques to carry out conventional infusion pump functions and operations, and such known aspects will not be described in detail here.

Figure 4:
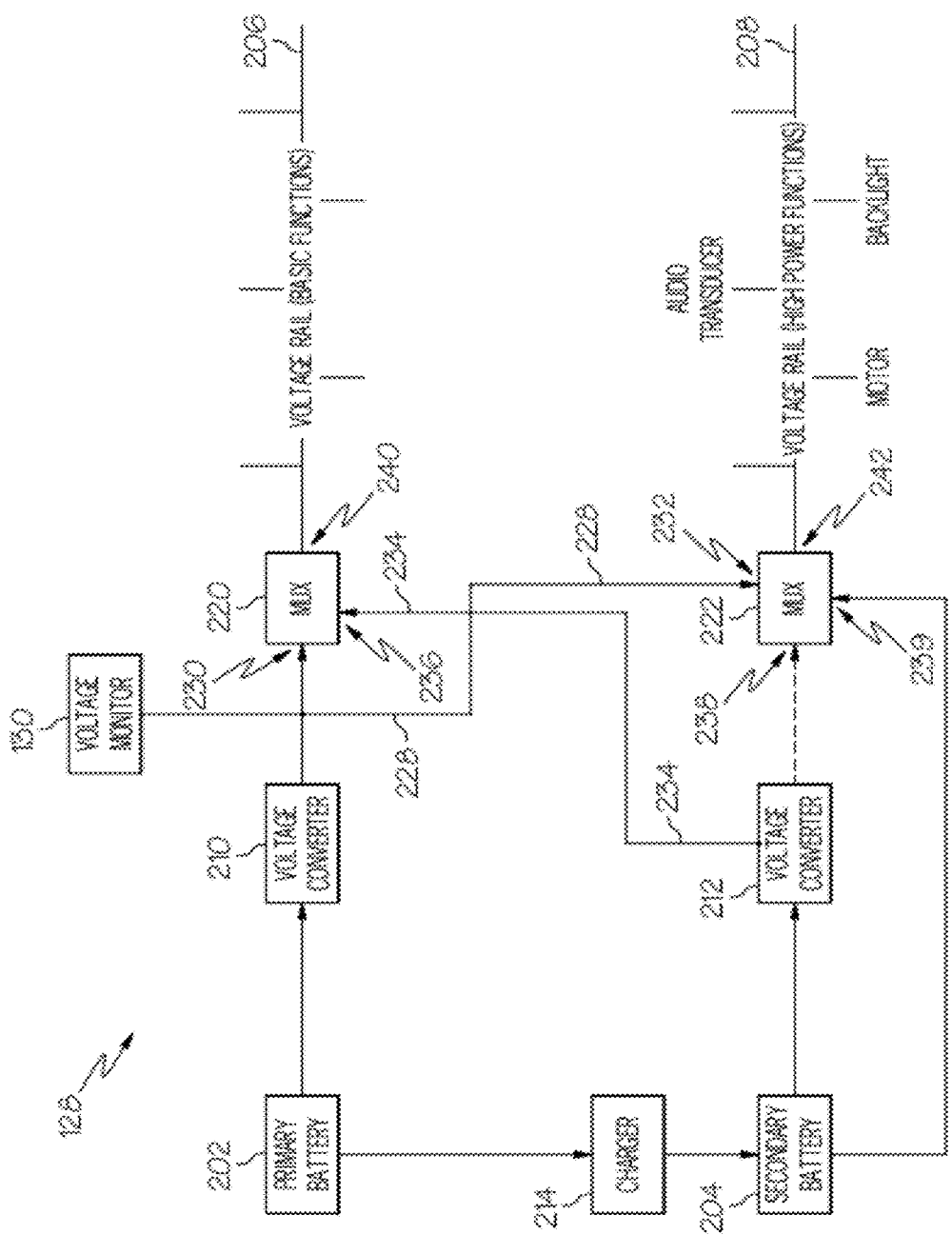
FIG. 4 is a schematic representation of an exemplary embodiment of a power distribution system suitable for use with an electronic device such as the fluid infusion device shown in FIG. 3.

As mentioned previously, the fluid infusion device 100 obtains its operating power from a primary battery and a secondary battery, which may be used independently or in conjunction with one another. The power distribution system 128 is controlled and manipulated in an appropriate manner such that the primary battery and the secondary battery support designated functions and operations of the fluid infusion device during specified power phases. In this regard, FIG. 4 is a schematic representation of an exemplary embodiment of the power distribution system 128. It should be appreciated that FIG. 4 depicts only one possible implementation of the power distribution system 128. Other embodiments of the host electronic device may utilize a power distribution system having a different architecture and topology than that shown in FIG. 4.

The illustrated embodiment of the power distribution system 128 includes or cooperates with a primary battery 202 and a secondary battery 204. The primary battery 202 will typically be a replaceable battery, such as an alkaline or a lithium AA size battery, while the secondary battery 204 will typically be a rechargeable battery. In practice, the secondary battery 204 may be considered to be a backup battery. Moreover, in certain embodiments the secondary battery 204 is internal to the fluid infusion device 100, and it is not accessible to the user. In other words, the secondary battery 204 may be a "permanent" and non-replaceable battery.

The power distribution system 128 includes a plurality of voltage rails, each of which is coupled to various elements, devices, modules, and features of the fluid infusion device 100. For the sake of simplicity, FIG. 4 depicts only two voltage rails: a voltage rail 206 to provide operating voltage for basic functions of the fluid infusion device 100; and another voltage rail 208 to provide operating voltage for high power functions of the fluid infusion device 100. As used here, basic functions represent relatively low power and/or relatively low current functions of the fluid infusion device 100, e.g., functions that might require less than about 50 mA of current. In contrast, high power functions represent relatively high power and/or relatively high current functions, e.g., functions that might require more than about 50 mA of current. Depending upon the specific requirements and features of the fluid infusion device 100, the power distribution system 128 may include one or more additional voltage rails, which may be designated as low power rails, high power rails, basic function rails, or as otherwise needed. Moreover, additional elements can be included in the power distribution system 128 to result in any alternate configuration needed to cooperate with additional voltage rails.

The illustrated embodiment of the power distribution system 128 also generally includes, without limitation: a voltage converter 210 associated with the primary battery 202; a voltage converter 212 associated with the secondary battery 204; a charger 214 for the secondary battery 204; a voltage multiplexer 220 for the voltage rail 206; and a voltage multiplexer 222 for the voltage rail 208. For ease of description, FIG. 4 also depicts the voltage monitor 130 even though it need not be considered to be a part of the power distribution system 128. For simplicity, FIG. 4 does not include reference (e.g., ground) voltage terminals, nodes, or connections for the elements and components of the power distribution system 128.

The primary battery 202 is coupled to both the input of the voltage converter 210 and the input of the charger 214. The output of the charger 214 is coupled to the secondary battery 204 to accommodate charging of the secondary battery 204 as needed. The secondary battery 204 is coupled to the input of the voltage converter 212. The output of the voltage converter 210 corresponds to a main voltage rail 228 of the fluid infusion device 100 (the main voltage rail 228 provides the main supply voltage for the fluid infusion device 100). The main voltage rail 228 is coupled to an input 230 of the voltage multiplexer 220 and to an input 232 of the voltage multiplexer 222. The output of the voltage converter 212 corresponds to a backup voltage rail 234 of the fluid infusion device 100. The backup voltage rail 234 is coupled to an input 236 of the voltage multiplexer 220. Accordingly, in the illustrated embodiment the voltage multiplexer 220 is coupled to the primary battery 202 via the voltage converter 210, and to the secondary battery 204 via the voltage converter 212.

In the illustrated embodiment, the secondary battery 204 is directly coupled to an input 239 of the voltage multiplexer 222. In alternate embodiments, however, the output of the voltage converter 212 may be coupled to an input 238 of the voltage multiplexer 222 (represented by the dashed arrow in FIG. 4). Accordingly, in the illustrated embodiment the voltage multiplexer 222 is coupled to the primary battery 202 via the voltage converter 210, and to the secondary battery 204 via a direct connection. The output 240 of the voltage multiplexer 220 is coupled to the "basic functions" voltage rail 206, and the output 242 of the voltage multiplexer 222 is coupled to the "high power functions" voltage rail 208. The voltage monitor 130 may be coupled to one or more voltage rails, nodes, and/or terminals of the power distribution system 128 as needed for voltage monitoring, measurement, and detection. For example, the voltage monitor 130 might be coupled to monitor the a voltage of the primary battery, a voltage of the secondary battery, an output voltage of the voltage converter 210, an output voltage of the voltage converter 212, etc. In certain implementations, the voltage monitor 130 is used to monitor the voltage present at the main voltage rail 228, as depicted in FIG. 4.

In certain embodiments, the primary battery 202 is a replaceable battery, such as a standard AA battery (alkaline, lithium, or the like). For such an implementation, the nominal voltage of the primary battery 202 will be about 1.5 volts. For this example, the secondary battery 204 is a rechargeable battery, such as a rechargeable lithium-ion battery. Although not always required, the secondary battery 204 may have a nominal voltage of about 3.7 volts. In practice, the primary battery 202 represents the main power supply of the fluid infusion device 100, and the secondary battery 204 represents the backup power supply of the fluid infusion device 100, as will be explained in more detail below.

The operation of the charger 214 may be controlled or regulated by one or more of the electronics, processor, and control module(s) 120 described above with reference to FIG. 3. In this regard, operation of the charger 214 is controlled to recharge the secondary battery 204 with the primary battery 202 as needed or desired. In other words, the energy of the primary battery 202 can be used to charge the secondary battery 204 (assuming that the primary battery 202 has sufficient energy to do so). To recharge the secondary battery 204, the charger 214 is turned on or is otherwise controlled into its active state so that energy from the primary battery 202 can be used to recharge the secondary battery 204.

The voltage converter 210 (which need not be included in all embodiments) converts the battery voltage of the primary battery 202 to a desired DC voltage level that is suitable for use as the main supply voltage on the main voltage rail 228. Depending on the nominal battery voltage and the specification for the main supply voltage, the voltage converter 210 may function to increase or decrease the battery voltage of the primary battery 202. For the exemplary embodiment described here, the voltage converter 210 boosts the nominal output voltage of the primary battery 202 (1.5 volts DC for this example) to the main supply voltage for the fluid infusion device 100 (which is about 3.26 volts DC for this example). The illustrated embodiment assumes that the main supply voltage serves as a common input to both voltage multiplexers 220, 222. If different voltages need to be routed to the different voltage rails 206, 208, then the voltage converter 210 (or more than one voltage converter) could be suitably configured to provide two or more supply voltages.

Similarly, the voltage converter 212 (which need not be included in all embodiments) converts the battery voltage of the secondary battery 204 to a desired DC voltage level that is suitable for use as the backup main supply voltage on the backup voltage rail 234. Depending on the nominal voltage of the secondary battery 204 and the specification for the backup main supply voltage, the voltage converter 212 may function to increase or decrease the battery voltage of the secondary battery 204. For the exemplary embodiment described here, the voltage converter 212 converts the nominal output voltage of the secondary battery 204 (3.7 volts DC for this example) to the backup main supply voltage for the fluid infusion device 100 (which is about 3.13 volts DC for this example). The illustrated embodiment assumes that the backup main supply voltage serves as one input to the voltage multiplexer 220, while the unconverted output of the secondary battery 204 serves as one input to the voltage multiplexer 222. In such an embodiment, the voltage converter 212 may be used to reduce the voltage of the secondary battery 204 before providing the reduced voltage to the input 236 of the voltage multiplexer 220 (for use with the "basic functions" voltage rail 206), while the unconverted output of the secondary battery 204 is directly used with the "high power functions" voltage rail 208. Of course, if additional voltages need to be routed to the different voltage rails 206, 208 and/or to other voltage rails, then the voltage converter 212 (or more than one voltage converter) could be suitably configured to provide two or more supply voltages.

In practice, the voltage output of the secondary battery 204 can be applied to the voltage rail 208 because some or all of the high power functions include or cooperate with respective power supplies, drivers, or voltage converters that are able to boost or reduce the voltage of the secondary battery 204 as needed. Accordingly, the architecture need not stage power supplies or voltage converters in series between the secondary battery 204 and the high power voltage rail 208. In contrast, the system is preferably designed such that the various basic functions can be driven with a common supply voltage present at the basic functions voltage rail 206.

The voltage multiplexer 220 is controlled to select one of its two input voltages as its output voltage for the voltage rail 206. Thus, in one operating state, the DC voltage present at the input 230 of the voltage multiplexer 220 corresponds to the DC voltage of the voltage rail 206. In the other operating state, the DC voltage present at the input 236 of the voltage multiplexer 220 corresponds to the DC voltage of the voltage rail 206. Similarly, the voltage multiplexer 222 is controlled to select one of its two input voltages as its output voltage for the voltage rail 208. Thus, in a first operating state, the DC voltage present at the input 239 of the voltage multiplexer 222 corresponds to the DC voltage of the voltage rail 208. In a second operating state, the DC voltage present at the input 232 of the voltage multiplexer 222 corresponds to the DC voltage of the voltage rail 208. Accordingly, the control and operation of the voltage multiplexers 220, 222 allows the primary battery 202 and the secondary battery 204 to be coupled in a selectable manner to the voltage rails 206, 208 as needed. In this context, the voltage multiplexers 220, 222 (individually and collectively) represent a selection architecture of the power distribution system 128, where the selection architecture is coupled to the voltage rail 206, the voltage rail 208, the primary battery 202, and the secondary battery 204. As explained above, the voltage converters 210, 212 may (but need not) appear as intervening elements coupled between the batteries 202, 204 and the voltage multiplexers 220, 222.

The voltage rail 206 provides the operating voltage for certain functions or elements of the fluid infusion device 100 (e.g., basic or low power functions). Such basic functions may include, without limitation: the electronics, processor, and control module(s) 120; a wireless transceiver; a display driver; sensors; flash memory; keypad lighting; light emitting diodes; etc. In contrast, the voltage rail 208 provides the operating voltage for other functions or elements of the fluid infusion device 100 (e.g., high power functions). Such high power functions may include, without limitation: operating the fluid delivery or drive motor 134; operating the display backlight element 124; operating the audio transducer element 126; etc. In this regard, the motor 134, the backlight element 124, and the audio transducer element 126 are coupled to the voltage rail 208 to obtain operating voltage (which may be supplied by the primary battery 202 or the secondary battery 204 depending upon the power phase of the fluid infusion device 100).

During operation of the fluid infusion device 100, one or more of the electronics, processor, and control modules 120 (see FIG. 3) regulates the operation of the power distribution system 128 in accordance with a plurality of different power phases that are intended to take better advantage of the energy capacity of the primary battery 202. The exemplary embodiment described here employs at least three distinct power phases (although more or less than three could be implemented in practice). During a first power phase, the primary battery 202 is coupled to the voltage rail 206 and to the voltage rail 208 to provide energy for the basic functions and the high power functions. During a second power phase, the primary battery 202 is coupled to the voltage rail 206 to provide energy for the basic functions, and the secondary battery 204 is coupled to the voltage rail 208 to provide energy for the high power functions. During the third power phase, the secondary battery 204 is coupled to the voltage rail 206 and to the voltage rail 208 to provide energy for the basic functions and the high power functions.

Figure 5:
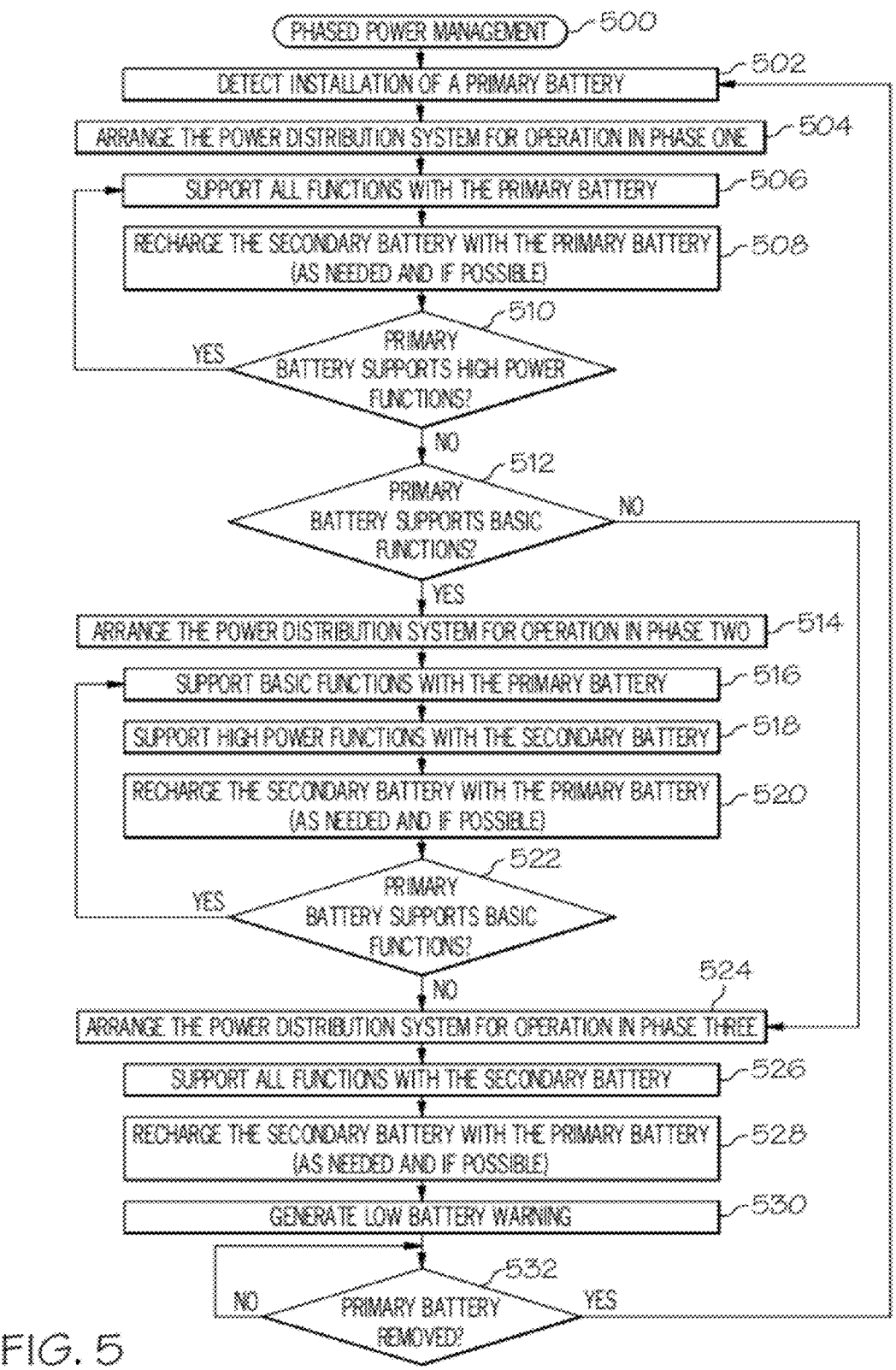
FIG. 5 is a flow chart that illustrates an exemplary embodiment of a phased power management process associated with the operation of an electronic device.

FIG. 5 is a flow chart that illustrates an exemplary embodiment of a phased power management process 500 associated with the operation of an electronic device, such as the fluid infusion device 100. The various tasks performed in connection with the process 500 (and other processes described herein) may be performed by software, hardware, firmware, or any combination thereof. For illustrative purposes, the following description of a given process may refer to elements mentioned above in connection with FIGS. 2-4. In practice, portions of a described process may be performed by different elements of the described system, e.g., a battery, a voltage multiplexer, a controller, processor, or electronics module, or the like. It should be appreciated that a described process may include any number of additional or alternative tasks, the tasks shown in the figures need not be performed in the illustrated order, and a described process may be incorporated into a more comprehensive procedure or process having additional functionality not described in detail herein. Moreover, one or more of the tasks shown in the figures could be omitted from an embodiment of a described process as long as the intended overall functionality remains intact.

The phased power management process 500 may be executed by an electronic device to increase the amount of energy that is extracted from its primary battery before replacement. This embodiment of the process 500 begins by detecting the installation of a new or replacement primary battery (task 502). Task 502 may involve the monitoring of the primary battery voltage to detect a condition that is indicative of the removal and/or replacement of a primary battery. For example, if a minimum voltage (e.g., 500 mV) is detected at the primary battery output, then the process 500 assumes that a primary battery is present. Accordingly, if the detected primary battery voltage falls below this threshold for a sufficient duration of time, then task 502 assumes that the primary battery has been removed. Thereafter, detection of a primary battery voltage above the threshold will signify that the primary battery has been replaced.

Although a "new" primary battery will typically be unused, the process 500 also contemplates the installation of a primary battery that has at least some of its energy depleted. In response to the installation of a primary battery, the power distribution system is arranged and configured to initially operate the device in the first power phase (task 504). During the first power phase, the primary battery provides the energy to support all of the functions of the device, including the basic functions and the high power functions (task 506). Moreover, the secondary battery is charged with the primary battery (as needed and if possible to do so) while the device is operating in the first power phase (task 508). This example assumes that the primary battery is able to support all of the functions for at least an initial period of time and, therefore, that the device is actually operated in the first power phase. During this period of time, the power distribution system is arranged such that the primary battery provides voltage for the "basic functions" voltage rail and the "high power functions" voltage rail. Accordingly, the secondary battery is disconnected from the two voltage rails for operation in the first power phase.

In certain embodiments, the main supply voltage (present at the main voltage rail) is monitored during operation of the electronic device, and the detected main supply voltage controls or otherwise influences the transition from one phase to another phase. In this regard, the power distribution system remains arranged in accordance with the first power phase when the main supply voltage is stable and greater than or equal to a stated threshold value. In practice, this threshold value may be selected based on the operating voltage and electrical current requirements and specifications of the components, devices, and elements coupled to the voltage rails. Thus, if the present state of the primary battery can provide sufficient energy to maintain the main power rail at a minimum voltage level required for the high power functions (given the electrical loading conditions at that time), then the process 500 assumes that it is safe to continue operating the device in the first power phase. For the example described here, the threshold value for the main supply voltage is within the range of about 3.050 to 3.100 volts, and is preferably about 3.075 volts. It should be appreciated that the nominal threshold value will be influenced by the specifications and nominal output voltage of the primary battery and/or the nominal output voltage of the voltage converter for the primary battery. For example, the exemplary threshold voltage range given above assumes that the nominal and expected output voltage of the voltage converter 210 is about 3.260 volts (see FIG. 4).

If the high power functions of the device are supported by the primary battery (query task 510), then the power distribution system will remain arranged in accordance with the first power phase. Referring again to FIG. 4, for the first power phase the voltage multiplexer 220 is controlled such that the voltage from the voltage converter 210 appears at the voltage rail 206, and the voltage multiplexer 222 is controlled such that the voltage from the voltage converter 210 also appears at the voltage rail 208. During the first power phase, the charger 214 may also be controlled as needed to charge the secondary battery 204 with the primary battery 202.

If the high power functions of the device are no longer supported by the primary battery (query task 510), then the process 500 may check whether the basic functions of the device are supported by the primary battery (query task 512). If the basic functions can be supported by the primary battery, then the power distribution system transitions from the first power phase to the second power phase. If the basic functions cannot be supported by the primary battery, then the power distribution system transitions from the first power phase to the third power phase, and the process 500 may proceed to a task 524 (described below).

The monitored main supply voltage may be analyzed to determine whether or not the basic functions can be supported by the primary battery. For this example, transitioning the power distribution system from the first power phase to the second power phase is triggered when the main supply voltage falls below the threshold value (while it is being monitored in the first power phase). Thus, the power distribution system can be arranged for operation in accordance with the second power phase (task 514) in response to a determination that the primary battery can no longer support the high power functions. If, after transitioning to the second power phase, the current state of the primary battery can provide sufficient energy to maintain the main power rail at the minimum voltage level, then the process 500 assumes that it is safe to continue operating the device in the second power phase.

During operation in the second power phase, the primary battery provides the energy to support the basic functions of device (task 516), while the secondary battery provides the energy to support the high power functions of the device (task 518). In addition, the secondary battery is recharged with the primary battery (as needed and if possible to do so) while the device is operating in the second power phase (task 520). For operation in the second power phase, the power distribution system is arranged such that the primary battery provides voltage for the basic functions voltage rail, and such that the secondary battery provides voltage for the high power functions voltage rail.

Referring again to FIG. 4, for the second power phase the voltage multiplexer 220 is controlled such that the voltage from the voltage converter 210 appears at the voltage rail 206, and the voltage multiplexer 222 is controlled such that the voltage from the secondary battery 204 appears at the voltage rail 208. This action also disconnects the primary battery 202 from the voltage rail 208. While operating in the second power phase, the charger 214 may also be controlled to as needed to charge the secondary battery 204 with the primary battery 202. Notably, the transition to the second power phase changes the load of the primary battery 202. Consequently, under normal conditions the monitored main supply voltage will increase to a level that is greater than the designated voltage threshold.

If the basic functions of the device are supported by the primary battery (query task 522), then the power distribution system will remain arranged in accordance with the second power phase. If, however, the basic functions of the device are no longer supported by the primary battery, then the power distribution system transitions from the second power phase to the third power phase. As mentioned above, if the monitored main supply voltage falls below the threshold voltage value while operating in the second power phase, then the process 500 assumes that the primary battery can no longer support even the basic functions. Consequently, the power distribution system is transitioned and arranged for operation in the third power phase (task 524). For this embodiment, transitioning the power distribution system from the second power phase to the third power phase is triggered when the main supply voltage falls below the threshold value (while it is being monitored in the second power phase).

During operation in the third power phase, the secondary battery provides the energy to support all functions of the device (task 526), including the basic functions and the high power functions. In other words, the electronic device does not rely on the primary battery for any of its operating functions. However, the primary battery may still be used to recharge the secondary battery (task 528) as needed and if possible to do so. Thus, any residual energy left in the primary battery could be used to charge the secondary battery.

In certain embodiments, the process 500 generates a low battery warning at the electronic device (task 530) in response to the transition from the second power phase to the third power phase. The low battery warning may be associated with an audible alert, a displayed message, an activated graphical icon, or the like. The low battery warning is intended to notify the user of the low battery condition and to remind the user to replace the primary battery with a fresh battery as soon as possible to avoid any device downtime.

For operation in the third power phase, the power distribution system is arranged such that the secondary battery provides voltage for both of the voltage rails. Referring again to FIG. 4, for the third power phase the voltage multiplexer 220 is controlled such that the voltage from the voltage converter 212 appears at the voltage rail 206, and the voltage multiplexer 222 is controlled such that the voltage from the secondary battery 204 appears at the voltage rail 208. This action effectively disconnects the primary battery 202 from both voltage rails 206, 208 during the third power phase. During the third power phase, the charger 214 may also be controlled as needed to charge the secondary battery 204 with the primary battery 202.

The third power phase may be maintained for a predetermined period of time that is based on the expected energy capacity of the secondary battery, assuming that the secondary battery by itself is responsible for the operation of the device. For example, the third power phase may timeout after a specified number of minutes or hours, e.g., ten hours. Thereafter, it may not be possible to support all of the normal operations of the device. Accordingly, the user will have the opportunity to replace the primary battery during the third power phase.

Notably, the phased power management technique described above enables the electronic device to prolong the useful life of the primary battery regardless of the specific type (chemistry) of battery used. Theoretically, up to 90% of the total energy of a new primary battery can be utilized if this power management scheme is implemented. Moreover, the power management scheme need not have advance knowledge of the installed battery type, and the electronic device need not rely on any empirical characterizations of different battery types.

In addition to the phased power management scheme described above, the fluid infusion device 100 may employ an intelligent methodology for monitoring and indicating the remaining life of the primary battery. In contrast to traditional approaches that rely solely on the battery voltage level or a coulomb counter, the battery life indicator of the fluid infusion device 100 is generated using a combination of operating parameters, and in a manner that results in an accurate and time proportional indication of remaining battery life.

Figure 6:
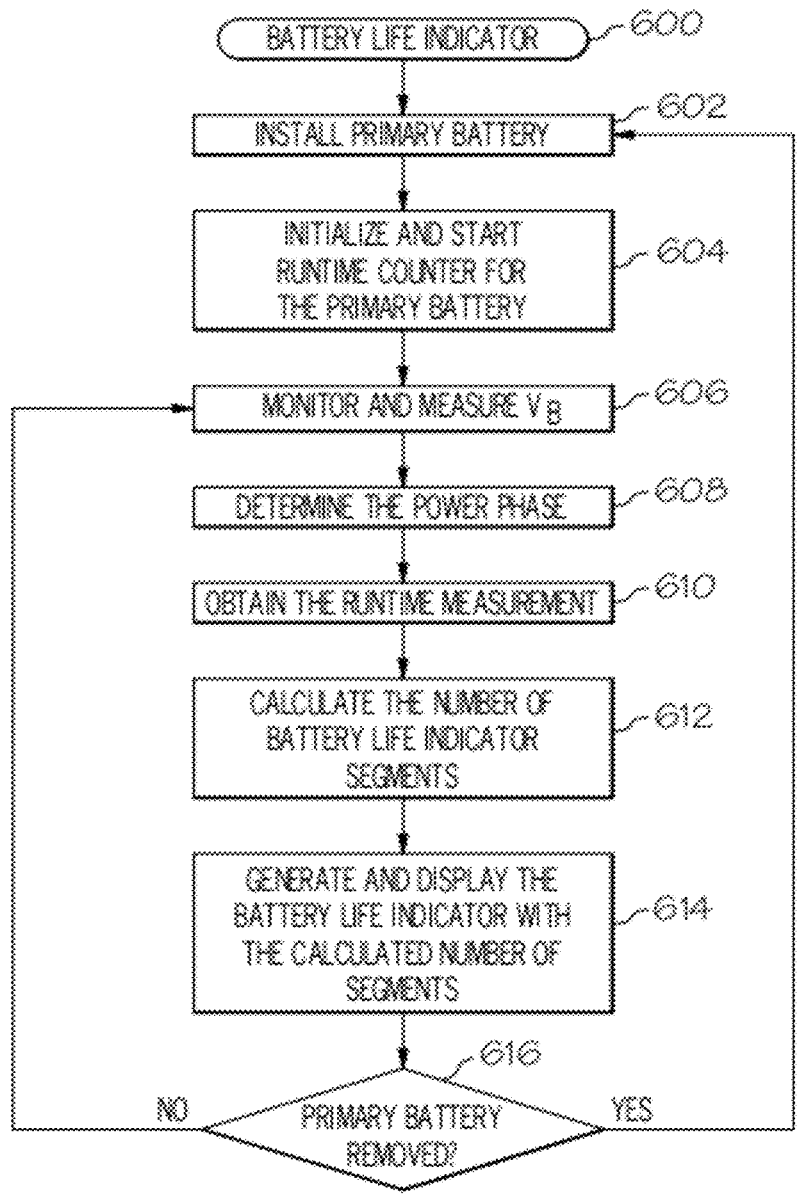
FIG. 6 is a flow chart that illustrates an exemplary embodiment of a battery life indicator process associated with the operation of an electronic device.

FIG. 6 is a flow chart that illustrates an exemplary embodiment of a battery life indicator process 600 associated with the operation of an electronic device, such as the fluid infusion device 100. Referring again to FIG. 3, a battery monitor system for the fluid infusion device 100 could be implemented with one or more of the electronics, processor, and control modules 120, which may cooperate with the voltage monitor 130, the battery runtime counter 132, and the power distribution system 128 for purposes of generating the battery life indicator 107.

This embodiment of the process 600 begins by detecting the installation of a new or replacement primary battery (task 602). Although a "new" primary battery will typically be unused, the process 600 also contemplates the installation of a primary battery that has at least some of its energy depleted. In response to the installation of a primary battery, the process 600 initializes and starts the runtime counter for the primary battery (task 604). In certain embodiments, task 604 is associated with the resetting or zeroing of the runtime counter, which may keep track of runtime in any desired unit (or units) of time, such as minutes, hours, or days. The process 600 monitors and measures a battery voltage, $V_B$, of the primary battery in an ongoing manner (task 606). The exemplary embodiment described here uses the voltage monitor to measure an "unloaded" battery voltage at a time when loading of the primary battery is at a minimum. In this regard, the unloaded primary battery condition might represent a state where the primary battery is loaded with only those components that are necessary to obtain the battery voltage reading (e.g., one or more of the modules 120, the voltage monitor 130, the memory 122, etc.). The measured battery voltage may be recorded or otherwise saved as appropriate.

In contrast to traditional approaches that use only the battery voltage as the metric for calculating remaining battery life, the technique described here also obtains at least one other operating parameter of the fluid infusion device (i.e., operating parameter(s) other than the battery voltage of the primary battery) and generates the battery life indicator based on the monitored battery voltage and the obtained operating parameter(s). The additional operating parameters considered by the process 600 may include, without limitation, a runtime measurement for the primary battery, and the power phase in which the device is currently operating (for the embodiment described above, the device operates in either a first power phase, a second power phase, or a third power phase). For this particular example, it is assumed that the indicating characteristics of the battery life indicator are controlled, governed, determined, or otherwise influenced by the power phase, the runtime measurement, and the monitored battery voltage of the primary battery. In alternate implementations, however, the characteristics of the battery life indicator might be controlled by: the power phase and the runtime measurement only; the power phase and the monitored battery voltage only; or the runtime measurement and the monitored battery voltage only. In other words, the amount of remaining battery life conveyed by the battery life indicator is governed by at least two of: the monitored battery voltage; the designated power phase; and the runtime measurement.

Assuming that the power phase of the device will be considered, the process 600 determines or otherwise obtains the power phase of the electronic device (task 608). For this example, therefore, task 608 determines whether the electronic device is operating in the first power phase, the second power phase, or the third power phase. The determined power phase may be recorded or otherwise saved as appropriate. The process 600 also obtains the runtime measurement of the primary battery (task 610) and records or saves the runtime measurement.

Referring again to FIG. 2, the illustrated embodiment of the battery life indicator 107 includes four segments that represent the remaining battery life of the primary battery. Alternatively, the battery life indicator 107 may be displayed, generated, annunciated, or otherwise presented to the user with appropriate characteristics that represent the remaining battery life. In other words, the use of a battery icon having four graphically distinct segments represents merely one of many possible embodiments for the battery life indicator 107. For a segmented battery life indicator such as that depicted in FIG. 2, the process 600 calculates the number of indicator segments to be displayed, illuminated, or otherwise rendered (task 612). Again, this particular embodiment calculates the number of segments based on the monitored battery voltage, the runtime measurement, and the power phase. Next, the process 600 generates and displays the battery life indicator with the calculated number of segments (task 614).

The amount of remaining battery life represented by one, two, three, four, or no icon segments may be designated or configured as appropriate for the particular embodiment. For this particular example, four segments indicates that about 67% to about 100% of the battery life remains, three segments indicates that about 33% to about 67% of the battery life remains, and two segments indicates that less than about 33% of the battery life remains. Thus, each of the "top" three segments approximately represents about one-third of the total battery life. Notably, only one segment displayed indicates a low battery condition corresponding to a maximum remaining runtime of about ten hours (or about 2% of remaining battery life). In other words, about ten hours of battery life remains when the battery life indicator 107 transitions from two segments to only one segment. For this particular embodiment, no segments displayed indicates an "end of battery life" condition corresponding to a maximum remaining runtime of about thirty minutes. Accordingly, only about thirty minutes of batter life remains when the battery life indicator 107 transitions from one segment to no segments.

If the primary battery is removed (query task 616), then the process 600 may begin again at task 602. If not, then most of the process 600 is repeated in an ongoing manner to update the battery life indicator in a continuous manner.

Figure 7:
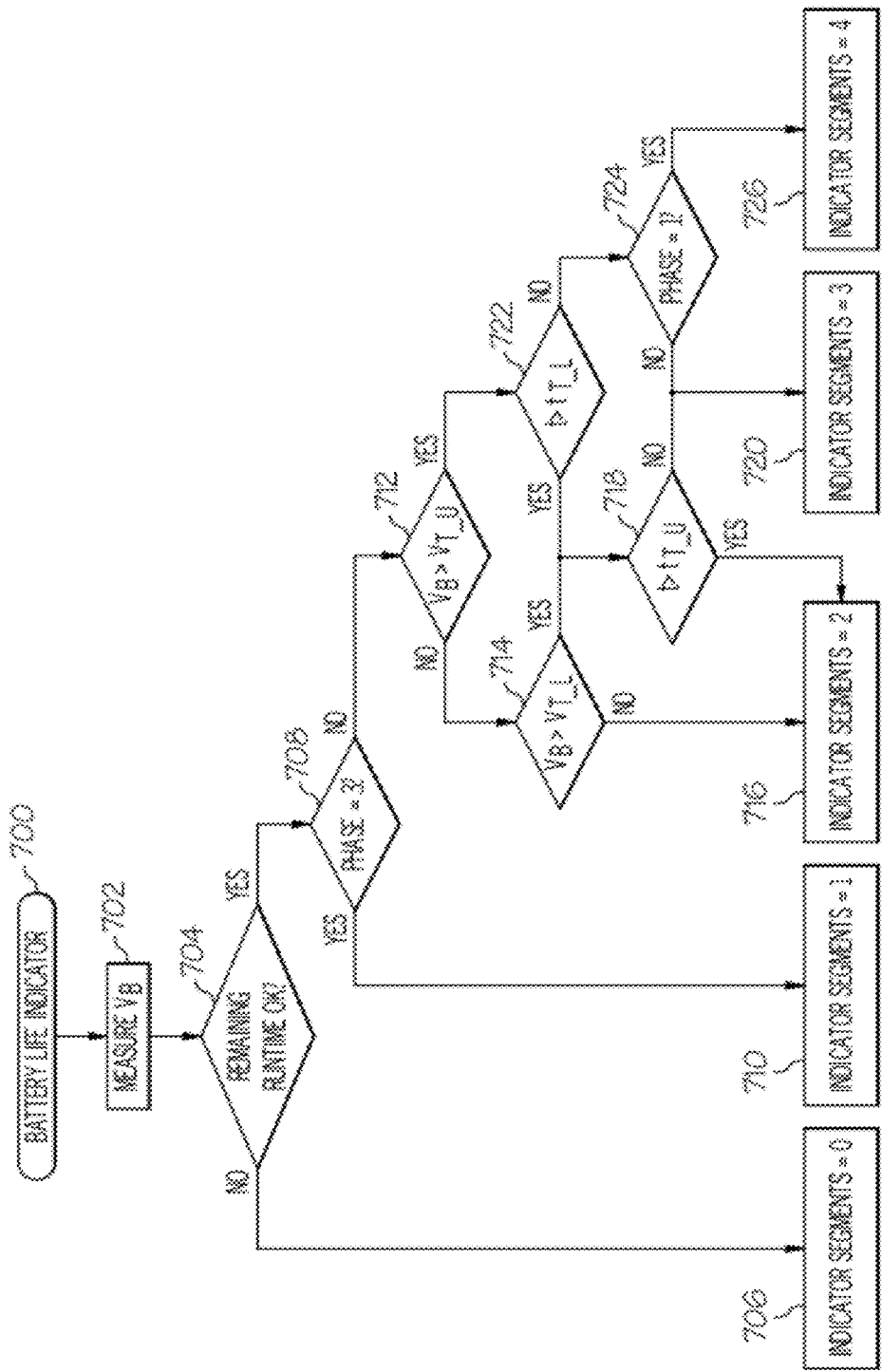
FIG. 7 is a flow chart that illustrates a particular embodiment of a battery life indicator process associated with the operation of an electronic device.

As mentioned in the context of the process 600, the number of battery life indicator segments may be determined based on two or more of: the monitored battery voltage, the runtime measurement, and the power phase of the device. In this regard, FIG. 7 is a flow chart that illustrates one particular embodiment of a battery life indicator process 700 associated with the operation of an electronic device such as the fluid infusion device 100. In practice, the process 700 may be incorporated into the process 600, and some aspects of the process 700 may be shared with the process 600.

The process 700 may be initiated whenever the battery voltage of the primary battery, $V_B$, is measured (task 702). For the exemplary embodiment described here, $V_B$ represents the voltage of the primary battery in an "unloaded" state, as explained in more detail above. In practice, task 702 may be performed periodically, in accordance with a predetermined schedule, or in accordance with the management of other processes, applications, and operations supported by the device. For example, it may be desirable to measure $V_B$ once a minute. In addition to task 702, the process 700 may perform an initial check to determine whether the operating state of the primary battery satisfies certain baseline criteria (query task 704). This embodiment checks whether the remaining runtime of the primary battery satisfies a threshold time period, such as thirty minutes. The threshold time period indicates that the primary battery is near its end of life. In practice, the determination made at query task 704 may be based on another process that is performed independently of the process 700, or it may be based on the current status of a variable maintained by the device. As another example, query task 704 might simply check whether the measured value of $V_B$ exceeds a minimum baseline voltage threshold.

If query task 704 determines that the primary battery does not have a sufficient amount of available runtime remaining, then the battery life indicator is generated such that no indicator segments are displayed (task 706). If query task 704 determines that the primary battery has at least a minimum amount of runtime remaining, then the process 700 checks whether the electronic device is currently operating in the third power phase (query task 708). If so, then the battery life indicator is generated such that only one indicator segment is displayed (task 710).

If the electronic device is not operating in the third power phase, then the process 700 continues by checking whether the monitored battery voltage ($V_B$) is greater than an upper threshold voltage value, $V_{T\_U}$ (query task 712). Notably, the same upper threshold voltage value is used for all primary battery types and chemistries, e.g., alkaline, lithium, or the like. In practice, $V_{T\_U}$ is selected in accordance with the expected nominal battery voltage, the operating requirements of the electronic device, and/or other operating parameters. More specifically, this threshold is selected after characterizing different battery types (AA size) and determining an accurate measure of full capacity or near-full capacity (i.e., at or near 100% life remaining). For the non-limiting example presented here, $V_{T\_U}$=1.3 volts DC. If the currently measured value of $V_B$ is less than or equal to $V_{T\_U}$ (the "NO" branch of query task 712), then the process 700 checks whether $V_B$ is greater than a lower threshold voltage value, $V_{T\_L}$ (query task 714). The same lower threshold voltage value may be used for all primary battery types and chemistries. In practice, $V_{T\_L}$ is selected in accordance with the expected nominal battery voltage, the operating requirements of the electronic device, and/or other operating parameters. More specifically, this lower threshold is selected after characterizing different battery types and determining a voltage that generally indicates some decay or a typical amount of energy consumption. For the non-limiting example presented here, $V_{T\_L}$=1.2 volts DC. If the currently measured value of $V_B$ is less than or equal to $V_{T\_L}$ (the "NO" branch of query task 714), then the battery life indicator is generated such that only two indicator segments are displayed (task 716). Note that the upper and lower threshold values apply to different battery chemistries such that the process 700 can be universally executed without regard to the specific battery type that is currently installed.

Referring back to query task 714, if the currently measured value of $V_B$ is greater than $V_{T\_L}$ (the "YES" branch of query task 714), then the process 700 checks whether the runtime measurement (t) is greater than an upper threshold time value, $t_{T\_U}$ (query task 718). For this embodiment, the same upper threshold time value is used for all primary battery types and chemistries, e.g., alkaline, lithium, or the like. In practice, $t_{T\_U}$ is selected in accordance with the expected lifespan of a new primary battery, considering the variations associated with different battery types. The value of $t_{T\_U}$ may also be selected based on the number of segments in the battery life indicator and the desired manner in which the display of the segments is regulated. For the non-limiting example presented here, $t_{T\_U}$=14 days. If the currently obtained value of t is greater than $t_{T\_U}$ (the "YES" branch of query task 718), then the battery life indicator is generated such that only two indicator segments are displayed (task 716). If, however, the currently obtained value of t is less than or equal to $t_{T\_U}$ (the "NO" branch of query task 718), then the battery life indicator is generated such that only three indicator segments are displayed (task 720).

Referring back to query task 712, if the currently measured value of $V_B$ is greater than $V_{T\_U}$ (the "YES" branch of query task 712), then the process 700 continues by checking whether the runtime measurement (t) is greater than a lower threshold time value, $t_{T\_L}$ (query task 722). For this embodiment, the same lower threshold time value is used for all primary battery types and chemistries, e.g., alkaline, lithium, or the like. In practice, $t_{T\_L}$ is selected in accordance with the expected lifespan of a new primary battery, considering the variations associated with different battery types. The value of $t_{T\_L}$ may also be selected based on the number of segments in the battery life indicator and the desired manner in which the display of the segments is regulated. For the non-limiting example presented here, $t_{T\_L}$=4 days. If the currently obtained value of t is greater than $t_{T\_L}$ (the "YES" branch of query task 722), then the process 700 leads to query task 718 and continues as described above. If, however, the currently obtained value of t is less than or equal to $t_{T\_L}$ (the "NO" branch of query task 722), then the process 700 checks whether the device is currently operating in the first power phase (query task 724).

If the device is not operating in the first power phase (the "NO" branch of query task 724), then the battery life indicator is generated such that only three indicator segments are displayed (task 720). If, however, the device is operating in the first power phase (the "YES" branch of query task 724), then the battery life indicator is generated such that all four indicator segments are displayed (task 726).

The conditions and criteria associated with the exemplary process 700 may be summarized in the following manner. No segments are rendered if the remaining runtime of the primary battery is less than a designated time, or if the device otherwise indicates that the primary battery has failed, is completely or virtually void of charge, or the like. One (and only one) segment is rendered when the device is operating in the third power phase. Two (and only two) segments are rendered under three different scenarios: (a) when the electronic device is not operating in the third power phase, and $V_B \leq V_{T\_L}$; (b) when the electronic device is not operating in the third power phase, and $V_{T\_L} < V_B \leq V_{T\_U}$, and $t > t_{T\_U}$; or (c) when the electronic device is not operating in the third power phase, and $V_B > V_{T\_U}$, and $t > t_{T\_U}$. Three (and only three) segments are rendered under three different scenarios: (d) when the electronic device is not operating in the third power phase, and $V_{T\_L} < V_B \leq V_{T\_U}$, and $t \leq t_{T\_U}$; (e) when the electronic device is not operating in the third power phase, and $V_B > V_{T\_U}$, and $t_{T\_L} < t \leq t_{T\_U}$; or (f) when the electronic device is operating in the second power phase, and $V_B > V_{T\_U}$, and $t \leq t_{T\_L}$. Finally, all four segments are rendered when the electronic device is operating in the first power phase, and $V_B > V_{T\_U}$, and $t \leq t_{T\_L}$.

Under typical and normal operating conditions, the battery life indication techniques described here result in predictable, accurate, and temporally proportional behavior. For example, if the normally expected lifespan of a fully charged primary battery is forty days, then each displayed indicator segment will roughly correspond to ten remaining days of battery life.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A power management method for an electronic device having a primary battery and a secondary battery, the method comprising:

operating the electronic device in a first power phase during which only the primary battery provides energy to support all functions of the electronic device, and during which the secondary battery is disconnected such that the secondary battery provides no energy to support functions of the electronic device;

operating the electronic device in a second power phase during which the primary battery provides energy to support only basic functions of the electronic device, and during which the secondary battery provides energy to support only high power functions of the electronic device; and operating the electronic device in a third power phase during which only the secondary battery provides energy to support all functions of the electronic device, and during which the primary battery is disconnected such that the primary battery provides no energy to support functions of the electronic device.

2. The method of claim 1, wherein operating the electronic device in the first power phase comprises recharging the secondary battery with the primary battery.

3. The method of claim 1, wherein operating the electronic device in the second power phase comprises recharging the secondary battery with the primary battery.

4. The method of claim 1, wherein operating the electronic device in the third power phase comprises recharging the secondary battery with the primary battery.

5. The method of claim 1, further comprising generating a low battery warning in response to operating the electronic device in the third power phase.

6. The method of claim 1, further comprising arranging a power distribution system of the electronic device to transition from the first power phase to the second power phase when the primary battery can no longer support the high power functions.

7. The method of claim 6, further comprising arranging the power distribution system to transition from the second power phase to the third power phase when the primary battery can no longer support the basic functions.

8. A power management method for an electronic device having a primary battery, a secondary battery, a voltage converter to convert an output voltage of the primary battery to a main supply voltage for the electronic device, a first voltage rail to provide operating voltage for basic functions of the electronic device, a second voltage rail to provide operating voltage for high power functions of the electronic device, and a power distribution system, the method comprising:

monitoring the main supply voltage during operation of the electronic device;

initially operating the power distribution system in a first power phase such that only the primary battery provides voltage for the first voltage rail and the second voltage rail, and such that the secondary battery is disconnected from the first voltage rail and the second voltage rail;

transitioning the power distribution system from the first power phase to a second power phase such that the primary battery provides voltage only for the first voltage rail, and such that the secondary battery provides voltage only for the second voltage rail, wherein transitioning from the first power phase to the second power phase is triggered when the main supply voltage falls below a threshold value while monitored during the first power phase; and transitioning the power distribution system from the second power phase to a third power phase such that only the secondary battery provides voltage for the first voltage rail and the second voltage rail, and such that the primary battery is disconnected from the first voltage rail and the second voltage rail, wherein transitioning from the second power phase to the third power phase is triggered when the main supply voltage falls below the threshold value while monitored during the second power phase.

9. The method of claim 8, further comprising recharging the secondary battery with the primary battery.

10. The method of claim 8, further comprising disconnecting the secondary battery from the first voltage rail and the second voltage rail for operation in the first power phase.

11. The method of claim 8, further comprising disconnecting the primary battery from the first voltage rail and the second voltage rail for operation in the third power phase.

12. The method of claim 8, further comprising generating a low battery warning in response to transitioning from the second power phase to the third power phase.

\* \* \* \* \*